US012599688B2

(12) United States Patent
Ghalili

(10) Patent No.: US 12,599,688 B2
(45) Date of Patent: Apr. 14, 2026

(54) ULTRAVIOLET LIGHT DECONTAMINATION ASSEMBLY

(71) Applicant: Epoch International Enterprises Inc., Fremont, CA (US)

(72) Inventor: Foad Ghalili, Fremont, CA (US)

(73) Assignee: Epoch International Enterprises Inc., San Jose, CA (US)

( * ) Notice: Subject to any disclaimer, the term of this patent is extended or adjusted under 35 U.S.C. 154(b) by 376 days.

(21) Appl. No.: 17/591,507

(22) Filed: Feb. 2, 2022

(65) Prior Publication Data

US 2022/0241447 A1 Aug. 4, 2022

(51) Int. Cl.
| | |
|---|---|
| *A61L 2/24* | (2006.01) |
| *A61L 2/10* | (2006.01) |
| *A61L 2/26* | (2006.01) |
| *G01J 5/00* | (2022.01) |

(52) U.S. Cl.
CPC .................. *A61L 2/24* (2013.01); *A61L 2/10* (2013.01); *A61L 2/26* (2013.01); *G01J 5/0025* (2013.01); *A61L 2202/11* (2013.01); *A61L 2202/14* (2013.01)

(58) Field of Classification Search
None
See application file for complete search history.

(56) References Cited

U.S. PATENT DOCUMENTS

| | | | | |
|---|---|---|---|---|
| 8,894,419 | B1 * | 11/2014 | Buelow | ................. H02J 7/0045 |
| | | | | 439/39 |
| 11,135,333 | B1 | 10/2021 | Sood et al. | |
| 2021/0316025 | A1 | 10/2021 | Cole | |

FOREIGN PATENT DOCUMENTS

| | | | | | |
|---|---|---|---|---|---|
| CN | 107692901 | A | * | 2/2018 | .............. A47J 47/16 |
| DE | 102011001094 | A1 | * | 9/2012 | .............. A61L 2/10 |
| DE | 202015001059 | U1 | * | 5/2015 | ........... E05B 1/0069 |
| EP | 3406269 | A1 | * | 11/2018 | ........... B08B 7/0057 |
| KR | 20160133119 | A | * | 11/2016 | ........... E05B 1/0069 |

* cited by examiner

*Primary Examiner* — Andrew Smyth
(74) *Attorney, Agent, or Firm* — Gordon Rees Scully & Mansukhani, LLP

(57) ABSTRACT

A new UVC sterilization device for elevator buttons, which comprises of several UVC LEDs on an enclosed polymer body, equipped with an infrared sensor to provide signals when an object comes within a certain distance, along with a controller printed circuit board that drives the unit by providing a constant current for the disinfection LEDs, as well as a battery. The infrared sensor is connected with the MCU control unit in the main body through the infrared detection unit. The MCU control unit is connected with the LEDs through the LED control unit. The main body is mounted on the elevator wall by two brackets. These brackets mechanically hold the main body in place and align the LED rays towards the buttons. The product is small and compact, easy to carry and install, and proven to be effective against microbes which would ultimately reduce bacterial and virus transmissions.

6 Claims, 3 Drawing Sheets

ULTRAVIOLET LIGHT DECONTAMINATION ASSEMBLY

The present disclosure relates to an ultraviolet light (UV) decontamination assembly that provides UVC sterilization, in particular to a new UVC LED sterilization device.

The COVID-19 outbreak has caused many people to be wary of contaminated objects or surface. It is possible for many pathogens such as the COVID-19 to be transmitted through contamination of commonly touched surfaces. Once the virus infects the human body, the infected person will show cold-like symptoms such as fever, pneumonia, and breathing difficulties which may cause death of patients. There is a need to effectively prevent spread of the virus. It is well-known that protection materials, such as face masks, can effectively protect the spread of virus between individuals by preventing airborne. However, with the rapid increase in the number of infected individuals, it is very difficult contamination of commonly touched surfaces such as doorknobs, or keypads in elevators. Thus, there is a demand to prevent viral transmission through contact transmission. It is vital to avoid contact transmission by disinfecting commonly touched objects. To control the spread of pathogens on keypads or doorknobs, a common solution is to clean and disinfect contaminated surfaces with various chemicals. However, chemical disinfection is both time and labor consuming, and is not always performed on these surfaces.

Ultraviolet radiation, specifically the wavelength of about 100-280 nm (Ultraviolet C or "UVC"), is commonly used to kill microorganisms in the air. Through research and development, UVC disinfection method is effective and easy to use. UVC lamp devices has been formally widely used in the areas of medical treatment, epidemic prevention, pharmaceutical industry and food industry and other relevant areas. UVC lamps may be used to kill most microbes, including bacteria and viruses. However, ultraviolet disinfection also has disadvantages. If humans are exposed for a prolonged amount of time without professional protective measures, it will have certain side effects on the skin due to its radiation. Human epidermis exposure to the UVC lamp may be done in order to disinfect the skin, however, prolonged exposure may cause redness, itching and desquamation symptoms, and constant frequent exposure under UVC light may lead to tumors or cancer. Therefore, UVC lamp disinfection is preferred in the absence of nearby humans. Due to the slow disinfection rate of ultraviolet light, there is a problem of utilizing UVC lamp systems when humans are nearby.

An object of the disclosed system is to provide a different and novel configuration in order to solve the problems discussed above. The disclosed configuration is an improved UVC lamp system that prevents unwanted human exposure to UVC light while efficiently decontaminating commonly touched surfaces to decrease the spread of microbial contamination. Specifically, the disclosed system is configured to provide an inventive UVC sterilization device that is small in size, easy to carry and install, and can quickly disinfect objects touched by virus and bacteria carriers, whilst reducing unnecessary human radiation and minimize any damage to human body. The improved system is described in more detail below.

BRIEF DESCRIPTION OF THE DRAWINGS

An object of the disclosed system is to provide an improved pretensioner system that reduces the likelihood of hot gases escaping the pretensioner. The improved system is described in more detail below.

DETAILED DESCRIPTION

In general, a UVC decontamination device or assembly configured to decontaminate or sterilize a surface is disclosed herein. The UVC decontamination device or assembly may include a tube housing and a controller located within the housing. A UVC-LED drive control unit is located within the housing and connected to the controller. A first UVC-LED bulb is also located within the housing and the housing includes a first opening that permits light to pass from the first UVC-LED bulb toward the surface. The UVC-LED drive control unit is configured to provide constant current to the first UVC-LED bulb. A first infrared sensor is located within the housing, and the infrared sensor is in communication with the controller via an infrared detection unit. The infrared detection unit is configured to send data received from the first infrared sensor to the controller. The controller may be configured to activate the first UVC-LED bulb depending on the data signals received from the first infrared sensor. The system may include two brackets each located at the ends of the tube housing configured to mount the tube housing adjacent to the surface. The data received from the sensor may correspond to an object touching the surface. According to an alternative embodiment, the controller may be configured to deactivate the first UVC-LED bulb after a predetermined amount of time has elapsed.

Figure 1:
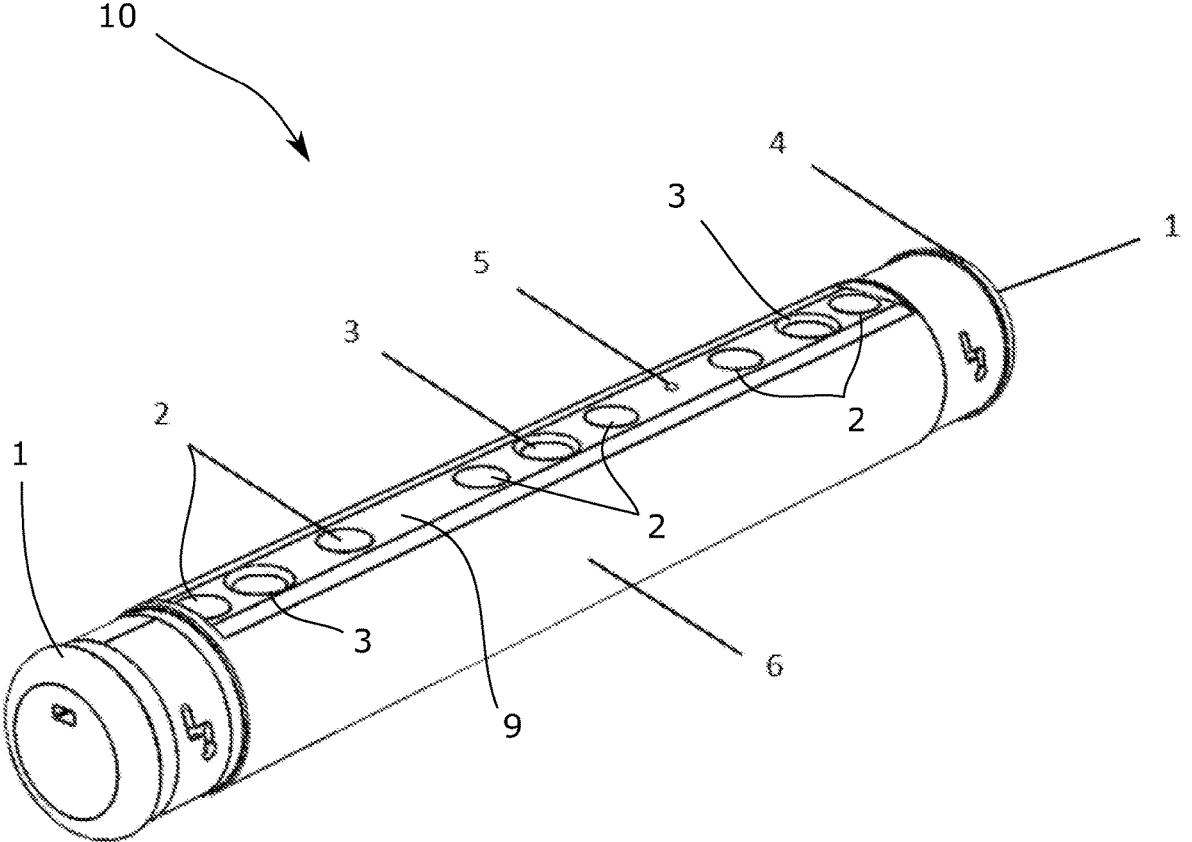
FIG. 1 shows an isometric view of a UVC-LED decontamination system.

FIG. 1 shows a UVC sterilization device 10, comprising a sealing plug 1, UVC-LED disinfection bulbs 2, infrared sensors 3, charging plug 4, status indicator light 5, and main tube body 6.

The UVC sterilization device 10 is a standalone wireless device with a rechargeable battery. The battery may be a lithium-ion battery or any other known small compact battery systems capable of fitting in the main tube body 6. The batteries may be connected in series. The main tube body 6 may be made of polymer and have for IP64 protection rating or higher. Since the sterilization device 10 includes a rechargeable battery the device is not required to be connected to an AC power supply and can be used in a variety of applications. It is equipped with a convenient charging plug 4 for quick charging. The charging plug 4 may be magnetic to facilitate a secure connection from the charger to the plug 4. The sealing plugs 1 may be located at the ends of the main tube body 6. The charging plug 4 may be located at one of the sealing plugs 1. In the exemplary embodiment shown, there is exactly six UVC-LED bulbs 2. The exact number and spacing of the bulbs may depend on the surface intended to be treated by the device 10. Infrared sensors 3 may be positioned between a set of UVC-LED bulbs 2. The main tube body 6 may include a groove 9. The infrared sensors 3 and UVC-LED bulbs 2 may be positioned within the groove 9. Both the infrared sensors 3 and UVC-LED bulbs may be positioned within the main tube body 6.

Figure 2:
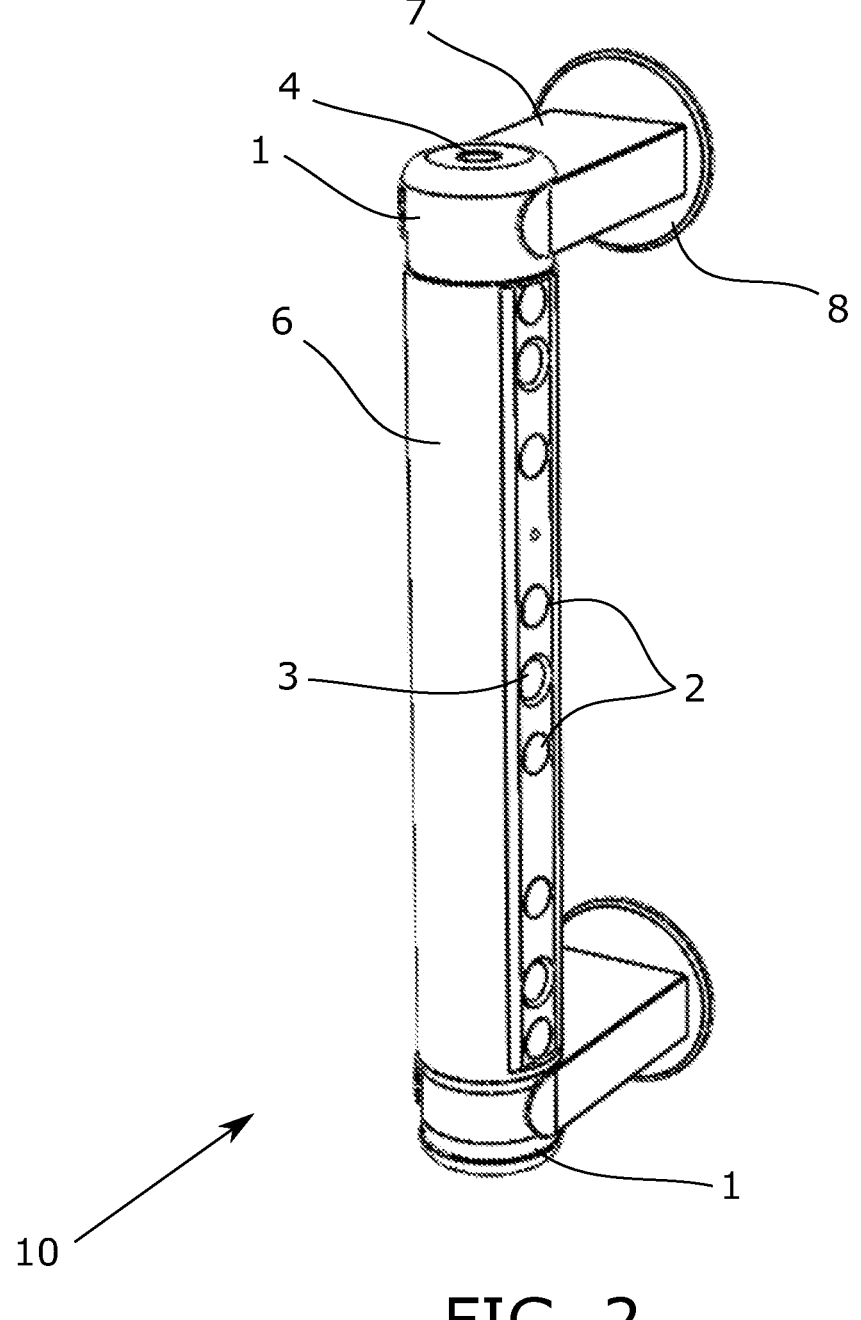
FIG. 2 shows an isometric view of a UVC-LED decontamination system of FIG. 1.

FIG. 2 shows the UVC sterilization device 10 mounted on a bracket 7 and a base 8. The bracket and base are configured to allow the main tube body 6 to be mounted onto different surfaces. Brackets 7 mechanically hold the main body 6 in place and align the UVC-LED towards the selected surface that is required to be decontaminated (e.g. elevator keypad or doorknobs). The main body 6 may include mounting holes for installing the brackets 7. The UVC-LED bulbs 2 are arranged inside the disinfection tube body 6 to ensure the optimal position for decontamination of the selected surface.

Figure 3:
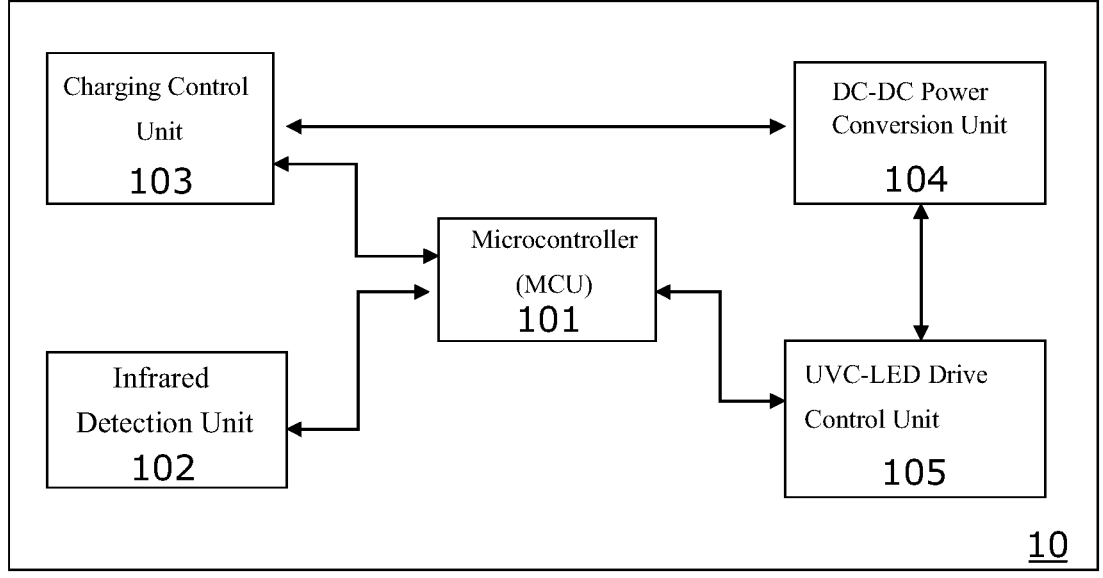
FIG. 3 is a schematic diagram of a UVC-LED decontamination system.

FIG. 3 shows an electronic schematic of the UVC sterilization device 10. A microcontroller (MCU) 101 is configured to communicate with a UVC-LED drive control unit 105, infrared detection unit 102. The UVC-LED drive control unit 105 may communicate with the UVC-bulbs 2 shown in FIG. 1 and FIG. 2. UVC-LED drive control unit 105 may be configured to provide constant current for the UVC-LED bulbs 2. The MCU 101 is configured to control the UVC-LED bulbs 2 via the drive control unit 105. Infrared sensors 3 are configured to communicate with the MCU 101 via the infrared detection unit 102.

The charging plug 4 is connected to a charging control unit 103. The charging unit may include a battery module configured to power the device 10. A DC-DC power conversion unit 104 is configured to provide the working voltage to the UVC-LED drive control unit 105 from the energy provided by the batteries in the charging control unit 103. The charging control unit 105 may further include a charging current control chip (e.g. CS5086 series produced by YONG HU KANG) and a booster circuit (e.g. LM1117 series produced by IT). The charging plug 4 may be configured to be connected with a charging interface to electrically connect to an outlet. Power from the outlet will travel to the boost circuit to increase the voltage from the charging interface (typically 5V) to the appropriate voltage for charging the battery. The batteries may be arranged in series. For example the batteries may be 3.7V lithium-lion batteries lithium providing appropriate power for the UVC-LED bulbs 2. These bulbs may be 3535 series produced by Longminas. The charging current control chip in the charging control unit 103 may be connected to the batteries and boost circuit. The charging current control chip may be configured to control the charging current and balance the two batteries to achieve the optimal use of the battery.

The status indicator light 5 may be connected to the MCU. The status indicator light 5 is used to show the battery state-of-charge (SOC). When the status indicator is green, it means the lithium battery is normal, and when it is red, it means the lithium battery is low. There is also a fixed hole with status indicator light on the disinfection tube body.

The infrared sensor 3 is configured to provide data signal(s) when an object comes within a predetermined distance, along with a controller printed circuit board that drives the unit by providing a constant current for the disinfection LEDs. The infrared sensor is connected with the MCU control unit in the main body through the infrared detection unit. The MCU control unit is connected with the LEDs through the LED control unit. The main body is mounted on the elevator wall by two brackets. The infrared sensor 3 is configured to detect human contact of the selected surface or objects proximate the selected surface. The infrared sensor 3 is configured to communicate sensor data representing the human contact to the MCU via the infrared detection unit. The MCU is configured to control the UVC-LED drive control unit 105 to activate the UVC-LED bulbs 2 in order to decontaminate the surface and/or objects, and, after a predetermined about of time, promptly turning off UVC-LED drive control unit in order to avoid unnecessary exposure. The infrared detection unit 102 (e.g. VCNL series infrared detection unit module produced by Weiss) may include an infrared emission circuit, an infrared receiving circuit, and a I2C interface circuit. The infrared emission circuit, infrared receiving circuit and I2C interface circuit are configured to be connected to each other. The I2C interface circuit of the infrared detection unit 102 is connected with the I2C interface of MCU (e.g. STM32F0 series produced by STMICROELECTRONICS). The I2C interface of the detection unit 102 and MCU 101 may be configured to communicate with each other in order to communicate sensor data from the infrared sensor 3 to the MCU.

The UVC-LED drive control unit 105 includes a voltage boost circuit, a current control circuit (can use NU501 series), and a protection circuit. The voltage boost circuit is connected may be connected to or integrated with the DC-DC power conversion unit 104, and the current control circuit is connected with the MCU 101, which can provide constant current drive for the UCV-LED bulbs 2.

The infrared sensors 3, infrared detection unit 102, microcontroller 101, LED drive control unit 105, and UVC-LED bulbs 2 communicate together such that only a certain set of UVC-LED bulbs may be activated when a portion of the selected surface is touched. For example, as shown in FIG. 2, each set of UVC-LED bulbs may correspond to a portion of an elevator keypad. When a person contacts the bottom portion of the elevator keypad, only the bottom two UVC-LED bulbs may be turned on. Similarly, only the middle two UVC-LED bulbs may be turned on if a person contacts the middle portion of the elevator keypad and only the top two UVC-LED bulbs may be turned on if a person contacts the top portion of the elevator keypad. The MCU may also be configured to turn off the UVC-LED bulbs when the UVC-LED bulbs are turned on via the infrared sensors 3/infrared detection unit 102. When the object (e.g. human hand) is detected by the infrared sensors 3/infrared detection unit 102 MCU communicates to the LED drive control unit 105 to turn off the corresponding LED bulbs to prevent unwanted UVC exposure to the object.

The UVC-LED bulbs 2 is configured to be controlled through the MCU. The sterilization effect is determined by the ultraviolet dose, which depends on the ultraviolet irradiation time (or exposure time) and power (e.g. irradiance), which can be calculated by the following formula: using appropriate irradiance, controlling exposure time to determine the sterilization effect:

$$Dose = irradiance * exposure\ time$$

Studies on virus and bacteria have found that a dose of 2-16 mJ/cm$^2$ can kill 99.9% of virus. The disclosed device herein is capable of accurately eliminating the virus by controlling the irradiance and exposure time of the UVC-LED bulbs. The device disclosed herein is small and compact, easy to carry and install, and is proven to be effective against microbes which would ultimately reduce bacterial and virus transmissions. The device can disinfect selected surfaces efficiently while reducing unnecessary human radiation thus minimizing the damage to human body, and maximizing safety via detection of human contact of objects through the system disclosed herein.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," etc.) are merely used to describe the orientation of various elements in the FIGURES. It should be noted that the orientation of various elements may differ according to other exemplary embodiments, and that such variations are intended to be encompassed by the present disclosure.

It is important to note that the construction and arrangement of the pretensioner as shown in the various exemplary embodiments is illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present disclosure.

6

What is claimed is:

1. An automated UVC-LED assembly for decontaminating a surface spaced apart from the assembly, the automated UVC-LED assembly comprising: a tube housing comprising a groove, a controller located within the housing;

a UVC-LED drive control unit located within the housing connected to the controller;

a plurality of UVC-LED bulbs located within the housing, wherein the groove includes a plurality of openings that permits light to pass from the plurality UVC-LED bulbs;

the UVC-LED drive control unit is configured to provide constant current to the plurality of UVC-LED bulbs;

a plurality of infrared sensors located within the housing, wherein each of the plurality of infrared sensors is in communication with the controller via an infrared detection unit;

the infrared detection unit is configured to send data received from at least one infrared sensor of the plurality of infrared sensors to the controller;

wherein each infrared sensor is positioned between a pair of corresponding UVC-LED bulbs of the plurality of UVC-LED bulbs, such that each infrared sensor is paired with the pair of corresponding UVC-LED bulbs, wherein the plurality of UVC-LED bulbs and the plurality of infrared sensors are aligned within the groove;

wherein the controller is configured to activate only the pair of corresponding UVC-LED bulbs of the plurality of UVC-LED bulbs depending on the data signals received by a corresponding adjacent infrared sensor that is paired with the corresponding UVC-LED bulb, such that each infrared sensor only controls its adjacent corresponding UVC-LED bulb; and wherein the plurality of UVC-LED bulbs are configured to emit UVC radiation through the plurality of openings and direct the UVC radiation towards the surface that is spaced apart from the assembly.

2. The UVC assembly of claim 1, wherein the data corresponds to an object touching the surface.

3. The UVC assembly of claim 1, wherein the controller is configured to deactivate the corresponding UVC-LED bulb after a predetermined amount of time has elapsed.

4. The UVC assembly of claim 1, further comprising a sealing plug at one end of the tube body.

5. The UVC assembly of claim 4, wherein the sealing plug includes a charging plug configured to power a battery located within the tube housing.

6. The UVC assembly of claim 5, wherein the charging plug is magnetic.

\* \* \* \* \*